(12) United States Patent
Brown et al.

(10) Patent No.: US 11,075,754 B2
(45) Date of Patent: Jul. 27, 2021

(54) UNIVERSAL PERSONAL MEDICAL DATABASE ACCESS CONTROL

(75) Inventors: Theresa M. Brown, Tucson, AZ (US); Nedlaya Yazzie Francisco, Tucson, AZ (US); Suguang Li, Tucson, AZ (US); Beth Ann Peterson, Tucson, AZ (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 2253 days.

(21) Appl. No.: 12/354,739

(22) Filed: Jan. 15, 2009

(65) Prior Publication Data
US 2010/0179831 A1 Jul. 15, 2010

(51) Int. Cl.
| | | |
|---|---|---|
| *H04L 9/08* | (2006.01) |
| *G06Q 10/06* | (2012.01) |
| *G06Q 40/08* | (2012.01) |
| *G16H 10/60* | (2018.01) |
| *G06F 19/00* | (2018.01) |

(52) U.S. Cl.
CPC ............. *H04L 9/088* (2013.01); *G06F 19/00* (2013.01); *G06Q 10/06* (2013.01); *G06Q 40/08* (2013.01); *G16H 10/60* (2018.01); *H04L 2209/88* (2013.01)

(58) Field of Classification Search
CPC ..... H04L 9/088; H04L 2209/88; G16H 10/60; G06F 19/00; G06Q 10/06; G06Q 40/08
USPC .................................................. 705/2, 3, 51
See application file for complete search history.

(56) References Cited

U.S. PATENT DOCUMENTS

| | | | |
|---|---|---|---|
| 6,256,737 B1 | 7/2001 | Bianco et al. | |
| 7,362,868 B2 | 4/2008 | Madoukh et al. | |
| 2002/0010679 A1* | 1/2002 | Felsher | 705/51 |
| 2003/0055824 A1 | 3/2003 | Califano | |

(Continued)

FOREIGN PATENT DOCUMENTS

WO 200109701 2/2001

OTHER PUBLICATIONS

National Research Council (US) Committee on Maintaining Privacy and Security in Health Care Applications of the National Information Infrastructure; 1997; For the Record Protecting Electronic Health Information, National Academies Press (US); Chapter 4, pp. 82-126 (Year: 1997).*

(Continued)

Primary Examiner — Evangeline Barr
(74) Attorney, Agent, or Firm — Griffiths & Seaton PLLC

(57) ABSTRACT

Various embodiments for configuring a medical database by a processor in communication with at least one storage device in a computing environment are provided. Medical data are assigned to a patient. A plurality of data types is organized for the medical data. Portions of each of the plurality of data types are designated as public and private data. A plurality of access levels is organized for the medical data. Each of the plurality of data types includes the plurality of access levels. A first access level of the plurality of access levels corresponds to the patient. The medical data is classified according to the plurality of data types, for each of the plurality of data types, according to the plurality of access levels, and according to one of the public and the private data. The medical data is encrypted in a hierarchical structure corresponding to each of the plurality of access levels.

17 Claims, 7 Drawing Sheets

(56) References Cited

U.S. PATENT DOCUMENTS

2005/0216313 A1* 9/2005 Claud et al. ............... 705/3

OTHER PUBLICATIONS

Gerome Miklau et al., :Controlling Access to Published Data Using Cryptography, ACM Digital Library, 2003, 12 pages.
Mark Evered, "Flexbile, Enterprise Access Control with Object-oriented View Specification," ACM Digital Library, 2003, 8 pages.
Martin Abadi et al., "Security Analysis of Cryptographically Controlled Access to XML Documents," 2008, 29 pages.

* cited by examiner

| | GENERAL 502 | DIAGNOSTIC 504 | MEDICAL PROFESSION 506 | INSURANCE 508 |
|---|---|---|---|---|
| Information | Public Info:<br>• Name<br>• Address<br>• Past Addresss<br>• Telephone<br>• Date of Birth<br>• Height<br>• Weight<br>• Family History<br>• Database Id<br><br>Private Info:<br>• Higher security information such as SSN | Public Info:<br>• MRIs<br>• X-Rays<br>• Blood Work<br><br>Private Info:<br>• Test results the individual deems too private for the general user. | Public Info:<br>• Diagnosis<br>• Ongoing treatments<br>• Medication<br>• Surgical History<br>• Action Plans<br><br>Private Info:<br>• Doctor Notes<br>• Anticipated treatment<br>• Probable outcomes | Public Info:<br>• EOB (Explanation of Benefit) records<br>• Correspondence<br><br>Private Info:<br>• Liability concerns<br>• Actuary Data<br>• Risk analysis<br>• Correspondence |
| Owner | Individual | Individual | Medical Professional | Insurance Company |
| Read Access | Public: Users with access to the database entry<br><br>Private: Access must be granted by the owning individual | Public: Users with access to the database entry<br><br>Private: Access must be granted by the owning individual | Public: Users with access to the database entry<br><br>Private: The Professional who wrote the entry and the users they grant read access | Public: Users with access to the database entry<br><br>Private: The Insurance Company only |
| Write Access | The individual themselves only.<br><br>The information may be updated as needed | Approved Medical Professionals.<br><br>The information may only be written once. | Approved Medical Professionals.<br><br>The information may be updated as needed. | Insurance Company.<br><br>The information may be updated as needed. |

FIG. 5

UNIVERSAL PERSONAL MEDICAL DATABASE ACCESS CONTROL

BACKGROUND OF THE INVENTION

Field of the Invention

The present invention relates in general to computers, and more particularly to a method, system, and computer program product for implementing and configuring user access controls for a universal personal medical database in a computing environment.

Description of the Related Art

A computer database is a structured collection of records or data that is stored in a computer system. The structure is achieved by organizing the data according to a database model. The model in most common use today is the relational model. Other models such as the hierarchical model and the network model use a more explicit representation of relationships.

Computer databases rely upon software to organize the storage of data. This software is known as a database management system (DBMS). Database management systems are categorized according to the database model that they support. The model tends to determine the query languages that are available to access the database. A great deal of the internal engineering of a DBMS, however, is independent of the data model, and is concerned with managing factors such as performance, concurrency, integrity, and recovery from hardware failures.

In the medical profession, medical databases have proliferated as a mechanism to store and retrieve patient health information, as well as ancillary health information related to the patient such as insurance information. The implementation of such databases also has raised growing concerns about accessibility and patient privacy.

SUMMARY OF THE INVENTION

Currently, individual medical databases may exist that may contain a patient's medical history as it relates to a particular group of doctors, hospitals, or insurance carriers. There has been, however, growing interest in consolidating medical history and ancillary information into a single, remotely accessible database in which a variety of persons and personnel may utilize. Such a larger database may include a variety of medical information for a particular individual, such as medical history, family history, past and current medical procedures, diagnostic materials, and even perhaps a personalized genome for the individual.

Such a large amalgamation of personal information necessarily requires appropriate accompanying privacy protections. Because such information would be accessed by a variety of persons and personnel in varying capacities, a methodology for access must also be implemented. In addition, the data storage requirements of such a large database must be addressed.

In view of the foregoing, a need exists for a mechanism by which a universal medical database system may be implemented that addresses the privacy, accessibility, and storage issues described above. Furthermore, other desirable features and characteristics of the present invention will become apparent from the subsequent detailed description of the invention and the appended claims, taken in conjunction with the accompanying drawings and this background of the invention.

Accordingly, in one embodiment, by way of example only, a method for configuring a medical database by a processor in communication with at least one storage device in a computing environment is provided. Medical data are assigned to a patient. A plurality of data types is organized for the medical data. Portions of each of the plurality of data types are designated as public and private data. A plurality of access levels is organized for the medical data. Each of the plurality of data types includes the plurality of access levels. A first access level of the plurality of access levels corresponds to the patient. The medical data is classified according to the plurality of data types, for each of the plurality of data types, according to the plurality of access levels, and according to one of the public and the private data. The medical data is encrypted in a hierarchical structure corresponding to each of the plurality of access levels.

In an additional embodiment, again by way of example only, a system for configuring a medical database utilizing a processor in communication with a data storage subsystem in a computing environment is provided. The system includes at least one storage device. A database server is in communication with the at least one storage device. The database server is adapted for assigning medical data to a patient, organizing a plurality of data types for the medical data, designating a first portion of each of the plurality of data types as public data, designating a second portion of each of the plurality of data types as private data, and organizing a plurality of access levels for the medical data, wherein each of the plurality of data types includes the plurality of access levels, a first access level of the plurality of access levels corresponding to the patient. The database server is further adapted for classifying the medical data according to the plurality of data types, for each of the plurality of data types, according to the plurality of access levels, and according to one of the public and the private data, and encrypting the medical data in a hierarchical structure corresponding to each of the plurality of access levels.

In an additional embodiment, again by way of example only, a computer program product for configuring a medical database by a processor in communication with at least one storage device in a computing environment is provided. The computer program product comprises a computer-readable storage medium having computer-readable program code portions stored therein. The computer-readable program code portions comprise a first executable portion for assigning medical data to a patient, a second executable portion for organizing a plurality of data types for the medical data, a third executable portion for designating a first portion of each of the plurality of data types as public data, a fourth executable portion for designating a second portion of each of the plurality of data types as private data, a fifth executable portion for organizing a plurality of access levels for the medical data, wherein each of the plurality of data types includes the plurality of access levels, a first access level of the plurality of access levels corresponding to the patient, a sixth executable portion for classifying the medical data according to the plurality of data types, for each of the plurality of data types, according to the plurality of access levels, and according to one of the public and the private data, and a seventh executable portion for encrypting the data in a hierarchical structure corresponding to each of the plurality of access levels.

In still another embodiment, again by way of example only, a database operational on a database server utilizing a processor in communication with at least one storage device in a computing environment is provided. The database includes medical data assigned to a patient. A plurality of data types is organized for the medical data. A first portion of each of the plurality of data types is designated as public data. A second portion of each of the plurality of data types is designated as private data. A plurality of access levels is organized for the medical data. Each of the plurality of data types includes the plurality of access levels. A first access level of the plurality of access levels corresponds to the patient. The medical data is classified according to the plurality of data types, for each of the plurality of data types, according to the plurality of access levels, and according to one of the public and the private data, and is encrypted in a hierarchical structure corresponding to each of the plurality of access levels.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 5 illustrates exemplary data types, access level controls, and public/private data categories in a medical database;

DETAILED DESCRIPTION OF THE DRAWINGS

The present description and claimed subject matter describe exemplary system, method, and computer program product embodiments for implementing and configuring a universal personal medical database in a computing environment. The illustrated embodiments incorporate configurable access levels (including a variety of controls), classifications of public and private data, and a variety of data types to facilitate a central medical database repository that is remotely accessible by a number of users (such as patient, medical professionals, and insurance personnel).

Organization of varying data types, public/private data distinctions, and the varied controls integrated into an encrypted hierarchy of access levels ensures that privacy is maintained. In some embodiments, owners of the medical data constitute at least a portion of the access levels. Further, in some embodiments, the universal database is hosted in a storage subsystem in which a specially configured controller unit serves as gatekeeper. This allows a large amount of data to be securely and efficiently stored and maintained.

In the following description, reference is made to the accompanying drawings which form a part hereof and which illustrate several implementations of the present invention. It is understood that other implementations may be utilized and structural and operational changes may be made without departing from the scope of the present invention.

Figure 1:
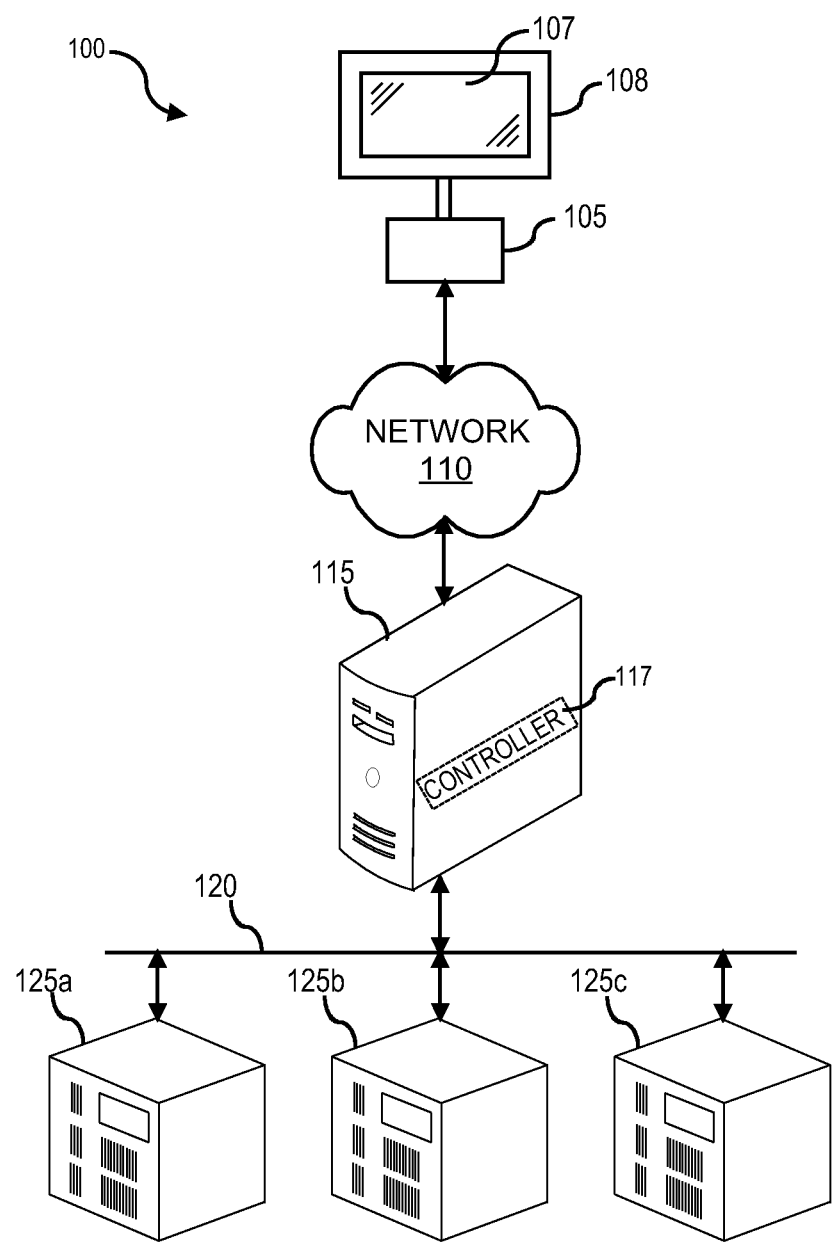
FIG. 1 is an exemplary computing environment.

FIG. 1 illustrates, in a block diagram, a computing environment 100 in accordance with certain implementations of the invention. Environment 100 includes a user interface device 105, such as a host, terminal, client, personal computer, personal desktop assistant (PDA), and the like. Device 105 includes an electronic display 108 that displays text or images on screen 107. The user interface device 105 may be utilized by a user, such as a database administrator, patient, hospital administrator, doctor, nurse, technician, insurance adjuster, and the like.

Device 105 is connected to network 110, a database server 117 (having a controller 115), a storage system network 120, and one or more storage devices 125. Although the environment 100 is depicted with one user interface device 105, one database server 115, one controller 117, and three storage devices 125, any number of user interface devices 105, servers 115, controllers 117, and storage devices 125 may be employed. In one embodiment, at least a portion of the system 100 comprises the IBM System Storage DS8000 series manufactured by International Business Machines ("IBM") of Armonk, N.Y.

Storage device 125 stores and retrieves data. For example, the storage device 125 may be a magnetic tape drive, hard disk drive, optical storage device, solid state storage device, and the like. Each storage device 125 is configured to store, retrieve, and maintain medical data. For example, primary universal medical data may be housed in a first storage device 125, while a backup for the data may be housed in an additional storage device 125.

Data on the storage devices 125 is provided to the database server 115, which uses hardware, software, firmware, or a combination thereof to implement the medical data stored on the one or more storage devices 125 as a universal database. In one embodiment, the database server 115 may combine data from one or more storage devices which is presented to the user interface device 105 as part of a virtual universal database. In other embodiments, the universal database may be imaged as such on one or more storage devices 125 themselves.

The controller 117 manages each storage device 125, communicating with the storage devices 125a-c through the storage subsystem network 120. The storage subsystem network 120 may be an Ethernet network, one or more fibre channel communication channels, or the like as is well known to those skilled in the art. In one embodiment, the controller 115 is configured as a center-of-room device, managing the plurality of storage devices 125 in the data storage system 100. For example, the controller 115 may manage bringing storage devices 125 on-line, taking storage devices 125 off-line, migrating data between storage volumes, initializing storage volumes, modifying firmware, performing diagnostic functions, and the like.

Figure 2:
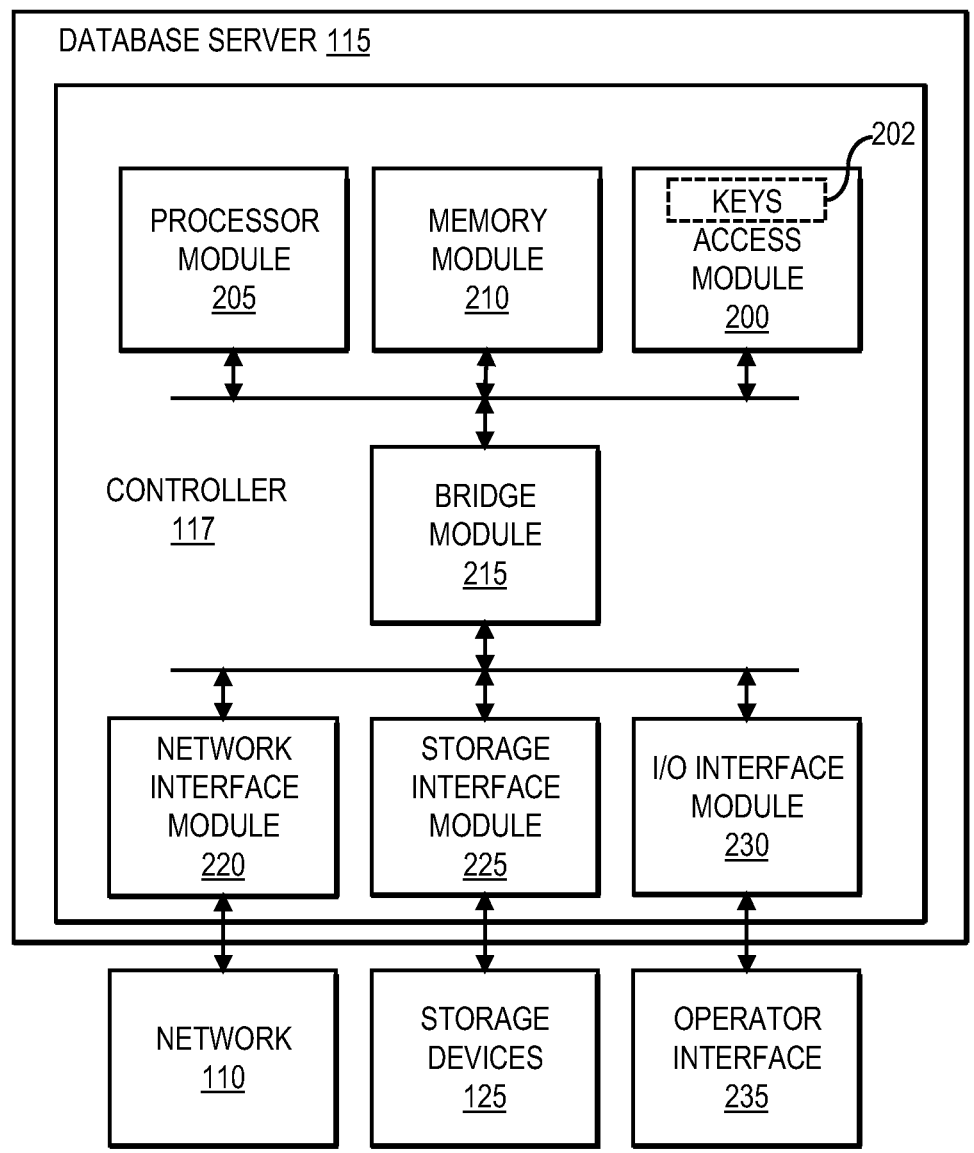
FIG. 2 is an exemplary database server operational in the exemplary computing environment depicted in FIG. 1.

FIG. 2 is a schematic block diagram illustrating one alternate embodiment of a controller 117 on database server 115. The depicted controller 117 may be one embodiment of the controller 115 of FIG. 1. The controller 117 includes an access module 200 incorporating encryption key functionality (keys 202), a processor module 205, a memory module 210, a bridge module 215, a network interface module 220, a storage interface module 225, and an input/output ("I/O") interface module 230. The controller 117 is depicted in communication with a network 110, a storage device 125, and an operator interface 235. The network 110, user interface device 105, and storage device 125 may be the network 110, user interface device 105, and storage device 125 of FIG. 1, previously.

Access module, processor module 205, memory module 210, bridge module 215, network interface module 220, storage interface module 225, and I/O interface module 230 may be fabricated of semiconductor gates on one or more semiconductor substrates. Each semiconductor substrate may be packaged in one or more semiconductor devices mounted on circuit cards. Connections between the access module 200, the processor module 205, the memory module 210, the bridge module 215, the network interface module 220, the storage interface module 225, and the I/O interface module 230 may be through semiconductor metal layers, substrate to substrate wiring, or circuit card traces or wires connecting the semiconductor devices.

The access module 200 may include a table of encryption keys 202, such as private encryption keys, that are used to validate encryption keys received from a user. Access module 200 may include hardware or firmware. Access module 200 may execute software that provides encryption and decryption functionality, and coordinate encryption functionality with other subcomponents such as memory module 210 or processor module 205. In one embodiment, access module 200 may implement a hierarchy of encryption consistent with a hiehrarchy of access levels organized in the medical database.

The memory module 210 stores software instructions and data including software instructions and data. The processor module 205 executes the software instructions and manipulates the data as is well known to those skilled in the art.

The processor module 205 communicates with the network interface module 220, the storage interface module 225, and the I/O interface module 230 through the bridge module 215. The network interface module 220 may be an Ethernet interface and connect with the network 110 over an Ethernet connection. The network 110 may comprise an Ethernet interface and a router that communicates with the service center 105 over an Internet connection as is well known to those skilled in the art.

In one embodiment, the storage interface module 225 is a Fibre Channel interface. The fibre channel interface may communicate with one or more storage devices 125 through a fibre channel cable, although for simplicity the storage interface module 225 is depicted in communication with one storage device 125. In a certain embodiment, the I/O interface module 230 comprises a universal serial bus ("USB") interface. The USB interface may communicate with the operator interface 235 comprising a USB compatible keyboard, mouse, and the like. The I/O interface module 230 may also comprise a graphics module and communicate with a display comprised by the operator interface 235.

Figure 3:
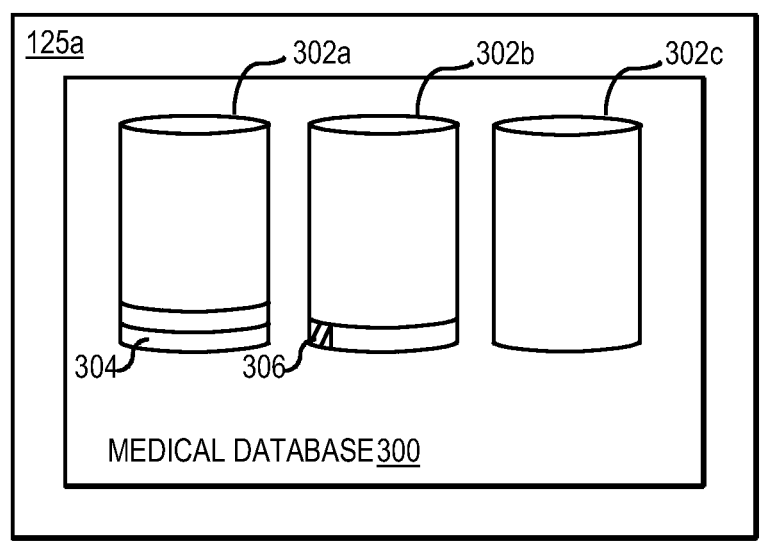
FIG. 3 is an exemplary medical database in a storage device.

FIG. 3 illustrates one example of a universal personal medical database 300 stored on a storage device 125a. Medical data used to populate the universal database 300 may be stored as datasets 306, tracksets 304, or as individual storage volumes 302a-c. The database 300 may use the basic structure of a hierarchical database, such as an information management system (IMS) database produced by IBM®.

Figure 4:
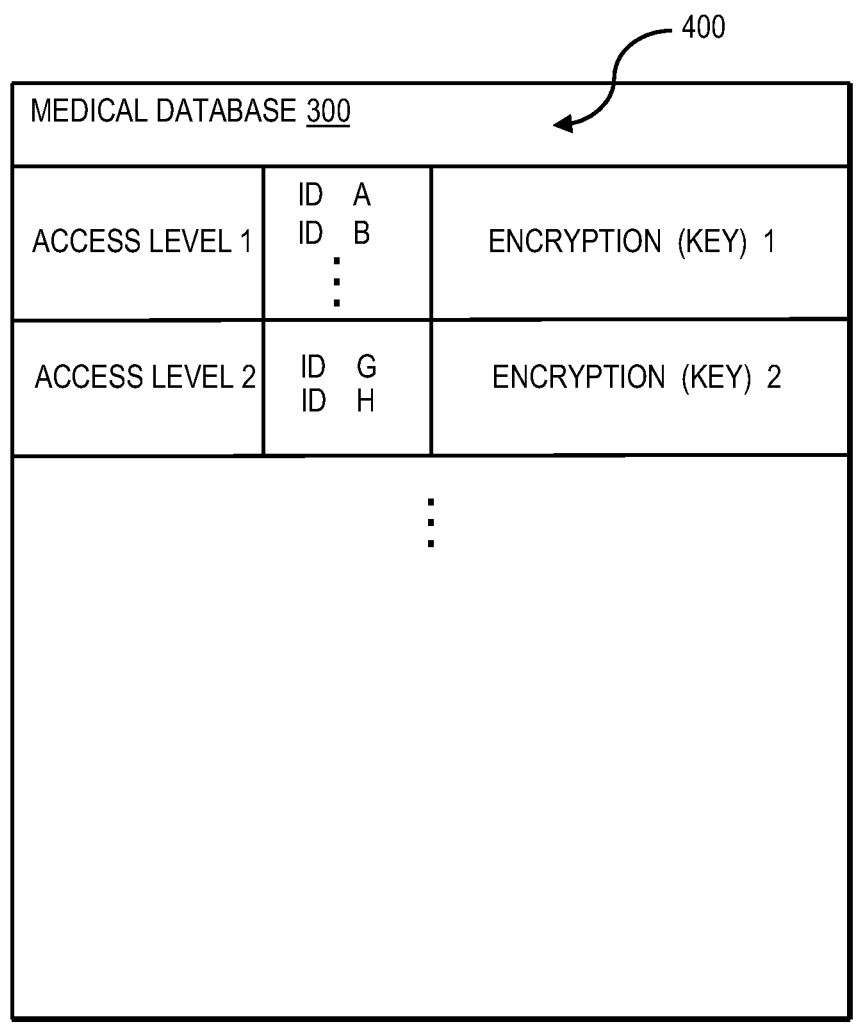
FIG. 4 illustrates exemplary access levels in a medical database.

FIG. 4 illustrates a table of access levels 400 that may be used by the access module 200 on database server 115 (FIG. 2). As the skilled artisan will appreciate, the table 400 may be used, in whole or in part, by various components of the controller 117 to facilitate access control to the medical data on storage devices 125 (again, FIG. 2). By limiting access control (for example, encryption key validation) to a hardware component directly affiliated with the data storage subsystem network 120 and storage devices 125, the security of the medical data is greatly improved.

Medical data is classified in the database 300 according to several access levels. Each of the access levels may contain one or more additional access controls. For example, controls for read access, write access, a number of times access is allowed, the contents allowed to be accessed, and the contents required to be accessed may all be implemented in a particular fashion in a particular access level. As illustrated in the depicted embodiment, each of the access levels is also associated with one or more user identification (ID). A user, such as a patient, may be assigned a particular user ID. The user ID of the patient may then be associated with a particular access level, and with a particular encryption key to allow access to the access level. In this way, the database 300 provides a hierarchical structure of access/encryption for various users. In other embodiments, two-factor authentication may be used to verify a particular user/allow access to a particular access level and/or asymmetric encryption methodologies may be implemented as part of this hierarchical structure of access.

To take the foregoing discussion further, consider the example of a laboratory technician (lab tech) user. The lab tech may be assigned a particular user ID, and associated with access level 2/encryption level 2. The lab tech may perform a magnetic resonance imaging (MRI) procedure on a patient. Because the lab tech has been assigned access level 2 (with a corresponding set of access controls), they are given write permission to add the MRI information once. Once the MRI information is written into the database, the read/write access controls incorporated into access level 2 prohibit the lab tech from reading/writing information again.

In some cases, information may be provided in accordance with an access level that redacts any information that would reveal patient identity. This level of access may be useful for academic researchers performing statistical analysis on a sample of individuals. As the skilled artisan will appreciate, a wide variety of access levels may be customized for a wide variety of individual users, such as health professionals, insurance personnel, government agencies, researchers, and the like.

By knowing that the data was controlled in a way acceptable for privacy and security purposes, a greater number of individuals may agree to the inclusion of medical data. By use of a data storage subsystem, the information may be provided to remote locations. A particular patient's medical information may be accessed using the environment 100 (FIG. 1) regardless of whether the patient is in a particular location. For example, the patient may live in a first location, but may experience a medical issue while on travel. In this way, the patient always has access to records no matter where the patient is physically located.

As an example, in one embodiment, an individual's database entry consists of general, diagnostic, medical professional, and insurance data types. The data in each type would have different access levels for the various users who are allowed to access the entry. Users could consist of the individual themselves, medical professionals (doctors, nurses, physician assistants, lab techs), and insurance personnel.

FIG. 5, following, illustrates an exemplary table 500 in which various data types, access levels, and public/private data classifications of medical data to be collectively organized into a universal medical database. Table 500 includes various medical data organized according to general data type 502, diagnostic data type 504, medical profession data type 506, and insurance data type 508. Portions of each of the illustrated data types are designated as public and private data as shown. In one embodiment, the owner of the data is given the authority to make the designations. Different entries of the same data type may be either public or private, such as insurance correspondence.

In addition, table 500 incorporates two access level controls, read access 510 and write access 512. Again, within each organized access level, various controls such as read access 510 and write access 512 controls may be implemented. Additional controls not shown include the number of times of allowed access, or specific allowable or restricted content.

Consider the following example of medical data classified in the general data type 502. The patient (individual) is designated as the data owner. Data such as a patient's name, address, past addresses, telephone, date of birth, height, weight, family history, or database ID may be classified as public information. Higher security information such as a social security number (SSN) may be designated as private data.

Continuing the example further, the read access control 510 allows access to the public data to those users with access to the database entry. For private data, access must be granted by the owning individual. Write access control 512 allows only individuals themselves to have write access to the medical data.

In an additional example, consider medical data classified in the medical profession data type 506. Information such as diagnosis, ongoing treatment, medication, surgical history, and action plans may be designated as public information. Higher security information such as doctor notes, anticipated treatment, and probable outcomes may be designated as private information. For public information users, with access to the database entry are given read access. For private information, the medical professional who authored the database entry and the users they grant are given read access. Only approved medical professionals are given write access to update information as may be needed (such as a change to a diagnosis or treatment plan).

Figure 6:
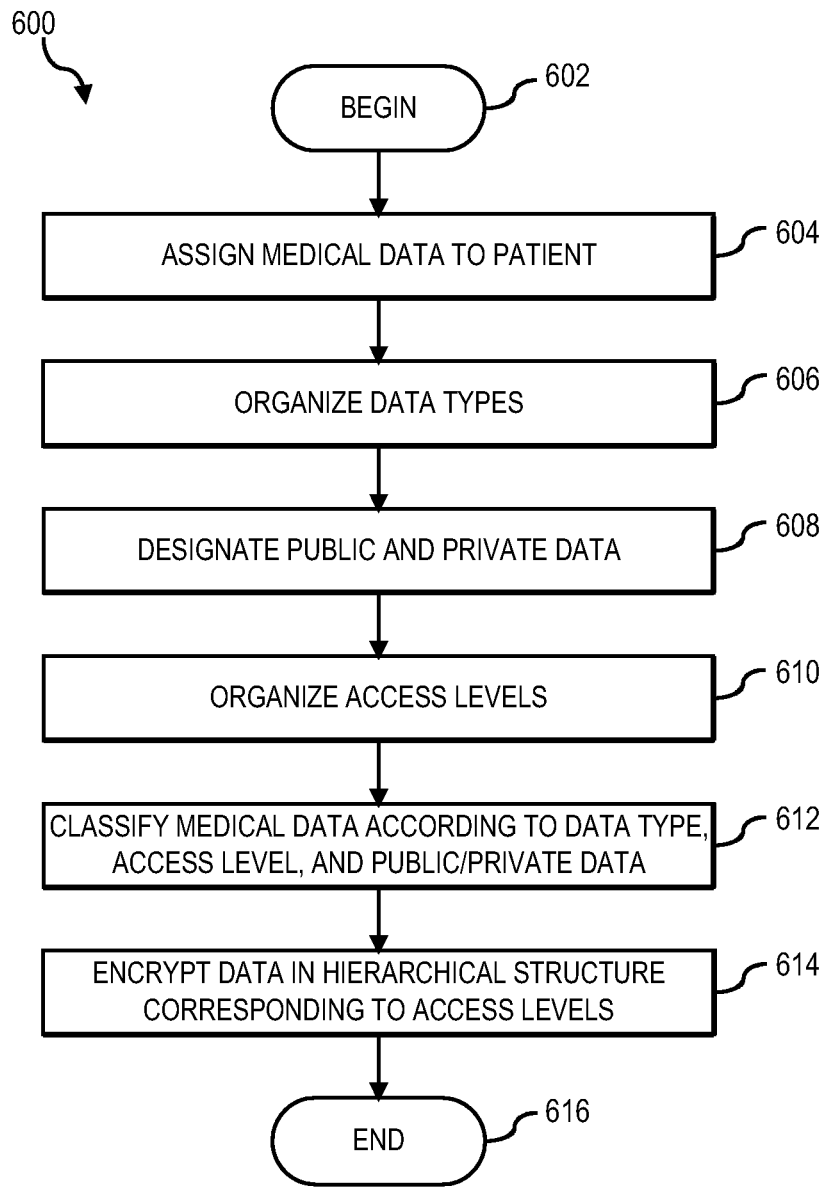
FIG. 6 is a flow chart of an exemplary method for configuring a universal medical database in a computing environment.
Figure 7:
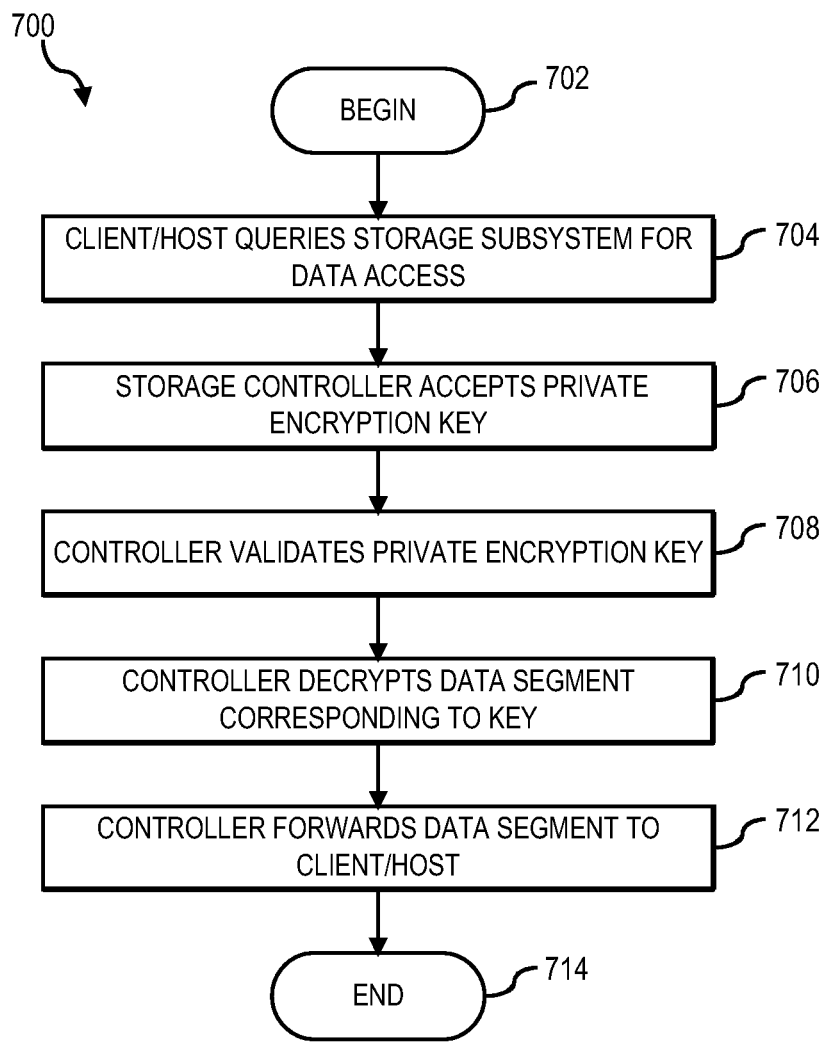
FIG. 7 is a flow chart of an exemplary method for providing access to medical data using a storage controller in a storage subsystem.

FIGS. 6 and 7 illustrate exemplary methods for configuring a universal personal medical database, and accessing medical data for such a database using a storage controller/storage subsystem, respectively. As one skilled in the art will appreciate, the described methods may be implemented by various means, such as hardware, software, firmware, or a combination thereof operational on or otherwise associated with the computing environment. For example, the methods may be implemented, partially or wholly, as a computer program product including a computer-readable storage medium having computer-readable program code portions stored therein. The computer-readable storage medium may include disk drives, flash memory, digital versatile disks (DVDs), compact disks (CDs), and other types of storage mediums.

Turning to FIG. 6, an exemplary method 600 for configuring a universal personal medical database in a computing environment is depicted Method 600 begins (step 602) with the assignment of medical data to a particular patient/individual (step 602). A number of data types, such as general, diagnostic, medical professional, and insurance data types, are organized (step 606). For each of the data types, portions are designated as public and private data (step 608).

Control then moves to step 610 where a number of access levels are organized (step 610). Here again, the access levels may correspond to the owner of the data type or the kind of user accessing the data. For example, a patient may be assigned in a particular access level. As a next step, various access controls for each levels may be assigned, such as particular read and write access controls for public and private data, or a number of times access is allowed.

As a next step, the medical data is classified according to data type, access level (including access level controls), and the public/private data designations previously described (step 612). Once the data is classified, it may then be encrypted in a hierarchical structure corresponding to the access levels organized. For example, in one embodiment, a number of encryption keys may be implemented to correspond with the same number of access levels. Once the medical data is encrypted (and decryption mechanisms are provided to users), then the method 600 ends (step 616).

Turning to FIG. 7, an exemplary method 700 for providing access to medical data using a storage controller in a storage subsystem is shown. Method 700 begins (step 702) with the client/host querying the storage subsystem for data access (step 704). Such a data query may be the result of a query from a patient, medical professional, insurance personnel, or a researcher from a remote location.

Control then moves to step 706, where the storage controller unit accepts a private encryption key. The key is then validated using the access module (step 706). The storage controller then decrypts a data segment (dataset, trackset, or storage volume) corresponding to the encryption key (step 710). The data segment is then forwarded from the storage subsystem to the client/host/user interface device (step 712). The method 700 then ends (step 714).

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Some of the functional units described in this specification have been labeled as modules in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

While one or more embodiments of the present invention have been illustrated in detail, the skilled artisan will appreciate that modifications and adaptations to those embodiments may be made without departing from the scope of the present invention as set forth in the following claims.

What is claimed is:

1. A method for configuring a medical database by a processor in communication with at least one storage device in a computing environment, comprising:
    amalgamating medical data assigned to a patient, from a plurality of individual medical databases remotely located from one another and each having respective access credentials, into a single, universally accessible database comprising the medical database, the medical database being stored on the at least one storage device and having a single access credential uniquely assigned to each of a plurality of users;
    organizing a plurality of access levels for the medical data assigned to the patient, wherein each of a plurality of data types are assigned to the medical data to include the plurality of access levels, a first access level of the plurality of access levels corresponding to the patient;
    encrypting the medical data in a hierarchical structure corresponding to each of the plurality of access levels by a storage controller comprising a hardware component controlling a remote data storage subsystem incorporating the at least one storage device, wherein at least one private encryption key is assigned to each of the plurality of access levels;
    storing the encrypted medical data by the storage controller within designated levels of the hierarchical structure on the at least one storage device;
    providing remote access to the plurality of users to access the medical database over a network through a graphical user interface via the storage controller, the storage controller acting as an encryption gatekeeper between the remote data storage subsystem and a host computer querying the medical database through the graphical user interface, wherein access restrictions to the encrypted medical data are applied according to each of the plurality of users having the at least one private encryption key respectively assigned to each of the plurality of access levels as the single access credential uniquely assigned to each of the plurality of users;
    upon remotely accessing the medical database over the network and authenticating the at least one encryption key by the storage controller, decrypting, by the storage controller, only a portion of the medical data corresponding to one of the plurality of access levels associated with the at least one encryption key;
    transmitting, by the storage controller, only the decrypted portion of the medical data across the network to the host computer; and
    displaying only the decrypted portion of the medical data on the graphical user interface on the host computer, wherein displaying only the decrypted portion of the medical data includes displaying content of the medical data corresponding to only the decrypted portion of the medical data on the graphical user interface according to which of the plurality of access levels the medical data is accessed under.

2. The method of claim 1, wherein organizing a plurality of data types for the medical data includes categorizing the medical data according to at least one of general, diagnostic, medical professional and insurance data types.

3. The method of claim 1, further including designating additional access levels to correspond to a plurality of medical and insurance personnel.

4. The method of claim 1, wherein organizing the plurality of access levels for the medical data includes implementing at least one of a read access control, a write access control, a number of allowed accesses, contents allowed to be accessed, and contents required to be restricted.

5. The method of claim 1, wherein encrypting the data in the hierarchical structure corresponding to each of the plurality of access levels is performed pursuant to an asymmetric encryption methodology.

6. The method of claim 1, further including granting access to the first access level pursuant to a two-factor authentication methodology implemented for the patient.

7. A system for implementing a medical database utilizing a processor in communication with a data storage subsystem, comprising:
    at least one storage device;
    a database server in communication with the at least one storage device, wherein the database server performs:
        amalgamating medical data assigned to a patient, from a plurality of individual medical databases remotely located from one another and each having respective access credentials, into a single, universally accessible database comprising the medical database, the medical database being stored on the at least one storage device and having a single access credential uniquely assigned to each of a plurality of users;
        organizing a plurality of access levels for the medical data assigned to the patient, wherein each of a plurality of data types are assigned to the medical data to include the plurality of access levels, a first access level of the plurality of access levels corresponding to the patient;
        encrypting the medical data in a hierarchical structure corresponding to each of the plurality of access levels by a storage controller comprising a hardware component controlling a remote data storage subsystem incorporating the at least one storage device, wherein at least one private encryption key is assigned to each of the plurality of access levels;
        storing the encrypted medical data by the storage controller within designated levels of the hierarchical structure on the at least one storage device;
        providing remote access to the plurality of users to access the medical database over a network through a graphical user interface via the storage controller, the storage controller acting as an encryption gatekeeper between the remote data storage subsystem and a host computer querying the medical database through the graphical user interface, wherein access restrictions to the encrypted medical data are applied according to each of the plurality of users having the at least one private encryption key respectively assigned to each of the plurality of access levels as the single access credential uniquely assigned to each of the plurality of users;
        upon remotely accessing the medical database over the network and authenticating the at least one encryption key by the storage controller, decrypting, by the storage controller, only a portion of the medical data corresponding to one of the plurality of access levels associated with the at least one encryption key;

transmitting, by the storage controller, only the decrypted portion of the medical data across the network to the host computer; and displaying only the decrypted portion of the medical data on the graphical user interface on the host computer, wherein displaying only the decrypted portion of the medical data includes displaying content of the medical data corresponding to only the decrypted portion of the medical data on the graphical user interface according to which of the plurality of access levels the medical data is accessed under.

8. The system of claim 7, wherein the medical data is organized according to at least one of general, diagnostic, medical professional and insurance data types.

9. The system of claim 7, wherein the database server is further adapted for designating additional access levels to correspond to a plurality of medical and insurance personnel.

10. The system of claim 7, wherein the database server is further adapted for implementing a plurality of controls corresponding to each of the plurality of access levels, wherein the plurality of controls includes at least one of a read access control, a write access control, a number of allowed accesses, contents allowed to be accessed, and contents required to be restricted.

11. A computer program product for configuring a medical database by a processor in communication with at least one storage device in a computing environment, the computer program product comprising a computer-readable storage medium having computer-readable program code portions stored therein, the computer-readable program code portions comprising:

a first executable portion for amalgamating medical data assigned to a patient, from a plurality of individual medical databases remotely located from one another and each having respective access credentials, into a single, universally accessible database comprising the medical database, the medical database being stored on the at least one storage device and having a single access credential uniquely assigned to each of a plurality of users;

a second executable portion for organizing a plurality of access levels for the medical data assigned to the patient, wherein each of a plurality of data types are assigned to the medical data to include the plurality of access levels, a first access level of the plurality of access levels corresponding to the patient;

a third executable portion for encrypting the medical data in a hierarchical structure corresponding to each of the plurality of access levels by a storage controller comprising a hardware component controlling a remote data storage subsystem incorporating the at least one storage device, wherein at least one private encryption key is assigned to each of the plurality of access levels;

a fourth executable portion for storing the encrypted medical data by the storage controller within designated levels of the hierarchical structure on the at least one storage device;

a fifth executable portion for providing remote access to the plurality of users to access the medical database over a network through a graphical user interface via the storage controller, the storage controller acting as an encryption gatekeeper between the remote data storage subsystem and a host computer querying the medical database through the graphical user interface, wherein access restrictions to the encrypted medical data are applied according to each of the plurality of users having the at least one private encryption key respectively assigned to each of the plurality of access levels as the single access credential uniquely assigned to each of the plurality of users;

a sixth executable portion for, upon remotely accessing the medical database over the network and authenticating the at least one encryption key by the storage controller, decrypting, by the storage controller, only a portion of the medical data corresponding to one of the plurality of access levels associated with the at least one encryption key;

a seventh executable portion for transmitting, by the storage controller, only the decrypted portion of the medical data across the network to the host computer; and an eighth executable portion for displaying only the decrypted portion of the medical data on the graphical user interface on the host computer, wherein displaying only the decrypted portion of the medical data includes displaying content of the medical data corresponding to only the decrypted portion of the medical data on the graphical user interface according to which of the plurality of access levels the medical data is accessed under.

12. The computer program product of claim 11, wherein the first executable portion for organizing a plurality of data types for the medical data includes a ninth executable portion for categorizing the data according to general, diagnostic, medical professional, and insurance data types.

13. The computer program product of claim 11, further including a ninth executable portion for designating additional access levels to correspond to medical and insurance personnel.

14. The computer program product of claim 11, wherein the first executable portion for organizing the plurality of access levels for the medical data includes a ninth executable portion for implementing at least one of a read access control, a write access control, a number of allowed accesses, contents allowed to be accessed, and contents required to be restricted.

15. A medical database operational on a database server utilizing a processor in communication with at least one storage device in a computing environment, comprising:

medical data assigned to a patient;

a plurality of access levels organized for the medical data, wherein each of a plurality of data types assigned to the medical data include the plurality of access levels, a first access level of the plurality of access levels corresponding to the patient, wherein the medical data:

is amalgamated from a plurality of individual medical databases remotely located from one another and each having respective access credentials, into a single, universally accessible database comprising the medical database, the medical database being stored on the at least one storage device and having a single access credential uniquely assigned to each of a plurality of users;

is encrypted in a hierarchical structure corresponding to each of the plurality of access levels by a storage controller comprising a hardware component controlling a remote data storage subsystem incorporating the at least one storage device, wherein at least one private encryption key is assigned to each of the plurality of access levels for configuring the medical database, is stored by the storage controller within designated levels of the hierarchical structure on the at least one storage device, is remotely accessible to the plurality of users via access provided to the medical database over a network through a graphical user interface via the storage controller, the storage controller acting as an encryption gatekeeper between the remote data storage subsystem and a host computer querying the medical database through the graphical user interface, wherein access restrictions to the encrypted medical data are applied according to each of the plurality of users having the at least one private encryption key respectively assigned to each of the plurality of access levels as the single access credential uniquely assigned to each of the plurality of users, upon remotely accessing the medical database over the network and authenticating the at least one encryption key by the storage controller, is at least partially decrypted, wherein only a portion of the medical data corresponding to one of the plurality of access levels associated with the at least one encryption key is decrypted, is transmitted, by the storage controller across the network to the host computer, wherein only the decrypted portion of the medical data is transmitted to the host computer, and is at least partially displayed on the graphical user interface of the host computer, wherein only the decrypted portion of the medical data is displayed, and wherein at least partially displaying the medical data includes displaying content of the medical data corresponding to only the decrypted portion of the medical data on the graphical user interface according to which of the plurality of access levels the medical data is accessed under.

16. The medical database of claim 15, wherein the data types include at least one of general, diagnostic, medical professional and insurance.

17. The medical database of claim 15, wherein each of the plurality of access levels further includes at least one of a read access control, a write access control, a number of allowed accesses, contents allowed to be accessed, and contents required to be restricted.

* * * * *